United States Patent [19]

Uyeo

[11] Patent Number: 4,960,880
[45] Date of Patent: Oct. 2, 1990

[54] ALKENYLSILYLAZETIDINONE INTERMEDIATES FOR CARBAPENEMS

[75] Inventor: Shoichiro Uyeo, Kyoto, Japan

[73] Assignee: Shionogi & Co., Ltd., Osaka, Japan

[21] Appl. No.: 247,264

[22] Filed: Sep. 21, 1988

[30] Foreign Application Priority Data

Sep. 22, 1987 [JP] Japan ................... 62-238066

[51] Int. Cl.⁵ ................. C07D 205/08; C07D 401/12; C07D 403/12; C07F 7/10
[52] U.S. Cl. ................... 540/200; 540/357; 540/361
[58] Field of Search ......................... 540/200

[56] References Cited

PUBLICATIONS

Carter, J. Organic Chem. 50, 3438 (1985).

Primary Examiner—Mark L. Berch
Attorney, Agent, or Firm—Wenderoth, Lind & Ponack

[57] ABSTRACT

An intermediate for synthesizing carbapenems is produced through
(1) a reaction of 4-(leaving group substituted)-2-azetidinone (I) with (alk-2-enyl)halosilane (II) to afford 4-(leaving group substituted)-1-(alk-2-enyl)silyl-2-azetidinone (III) and then
(2) a reaction of the product 4-(leaving group substituted)-1-alk-2-enyl)silyl-2-azetidinone (III) with acid to give the corresponding 4-(alk-2-enyl)-2-azetidinone (IV).

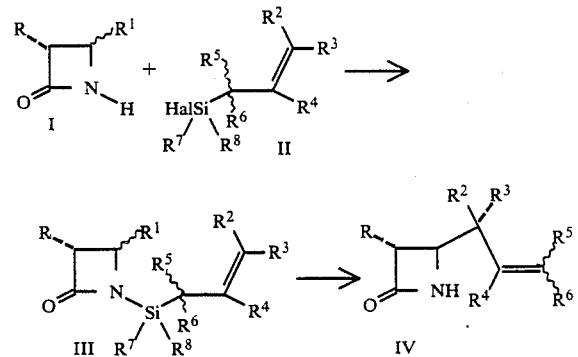

(The symbols are defined in the specification)

4 Claims, No Drawings

ALKENYLSILYLAZETIDINONE INTERMEDIATES FOR CARBAPENEMS

This invention relates to a stereospecific process for preparing an intermediate for synthesizing beta-lactam compounds which comprises the following two novel reactions, namely:

(1) reaction of 4-(leaving group substituted)-2-azetidinone (I) with (alk-2-enyl)halosilane (II) to afford 4-(leaving group substituted)-1-(alk-2-enyl)silyl-2-azetidinone (III) and (2) reaction of 4-(leaving group substituted)-1-(alk-2-enyl)silyl-2-azetidinone (III) with acid to give the corresponding 4-(alk-2-enyl)-2-azetidinone (IV).

More specifically this invention provides:

(1) a new process for producing 4-(leaving group substituted)-1-(alk-2-enyl)silyl-2-azetidinone (III) by treating 4-(leaving group substituted)-2-azetidinone (I) with (alk-2-enyl)halosilane (II);

(2) a new process for producing 4-(alk-2-enyl)-2-azetidinone (IV) by treating an 4-(leaving group substituted)-1-(alk-2-enyl)silyl-2-azetidinone (III) with acid; and (3) a new 4-(leaving group substituted)-1-(alk-2-enyl)silyl-2-azetidinone (III).

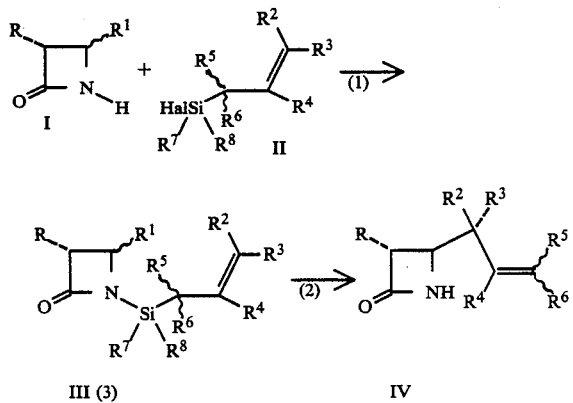

(wherein,
R is hydrogen or optionally substituted alkyl;
$R^1$ is a leaving group;
$R^2$ and $R^3$ each is hydrogen or optionally substituted alkyl or aryl;
$R^4$ is hydrogen, optionally substituted alkyl, or a nucleophilic group;
$R^5$ and $R^6$ each is hydrogen, optionally substituted alkyl or aryl, or optionally protected carboxy;
$R^7$ and $R^8$ each is hydrogen, halogen, or optionally substituted alkyl or aryl; and
Hal is halogen).

BACKGROUND OF THIS INVENTION

1-Alkylcarbapenems are in a sector of the recent topics in the field of chemotherapy. A promising known method for preparing a key intermediate, 4-(alk-2-enyl)-2-azetidinone (IV), is non-stereospecific (e.g., *J. Org. Chem.*, 50, 3438 (1985)) and the stereochemistry of the products can not be controlled to result in poor operability of the process and low yield of the objective 1-alkylcarbapenems.

SUMMARY OF THE INVENTION

This invention provides a stereospecific and industrial method by allylic rearrangement for producing 4-(alk-2-enyl)-2-azetidinone (IV), a key intermediate for producing antibacterial 1β-alkylcarbapenems and thus solving the problem found in the prior arts.

The reaction of 4-(leaving group substituted)-2-azetidinone (I) and (alk-2-enyl)halosilane (II) in the presence of an acid scavenger affords novel 4-(leaving group substituted)-1-(alk-2-enyl)silyl-2-azetidinone (III) under a mild condition. This product (III) gives the corresponding 4-(alk-2-enyl)-2-azetidinone (IV) by the action of acid. This product (IV) is a starting material for synthesizing 1-alkylcarbapenem.

The novel C to C bond formation proceeds intramolecularly but not intermolecularly under the same condition. Thus, 4-(leaving group substituted)-2-azetidinone (I) and (alk-2-enyl)halosilane (II) in the presence of zinc bromide failed to react giving 4-(alk-2-enyl)-2-azetidinone (IV). Furthermore, the stereospecific intramolecular alkenylation of 4-(leaving group substituted)-1-(alk-2-enyl)silyl-2-azetidinone (III) with acid is found to occur from the side opposite to the 3-side chain irrespective of the configuration of the 4-leaving group. As a result, 4-(alk-2-enyl)-2-azetidinone (IV) produced by the fissions of N to Si bond and Si to C bond with acid and subsequent aqueous work-up has the preferable 3,4-trans stereochemistry.

The intramolecular rearrangement of the 4-(leaving group substituted)-1-(alk-2-enyl)silyl-2-azetidinone (III) to give 4-(alk-2-enyl)-2-azetidinone (IV) is a sterically controlled sigmatropic reaction and therefore the stereochemistry of the product is uniform. Thus, this invention improve the production of objective carbapenem (e.g., with respect to the handling of the reaction mixture, especially purification, separation of isomer, time, and reagent in the work up) as compared with the prior art methods utilizing intermolecular reactions.

This invention is especially suitable for the following route for producing 1β-methylcarbapenems: Butadiene and dimethyldichlorosilane are reacted to afford dimethyl((Z)-but-2-enyl)chlorosilane (II) (e.g., *Izuvestia Academia Nauka USSR (Chemistry)*, 1980, page 2). This but-2-enylhalosilane (II) is reacted with a commercially available 3-(1-silyloxyethyl)-4-acetoxy-2-azetidinone (I) to produce 4-(leaving group substituted)-1-(alk-2-enyl)silyl-2-azetidinone (III). This 4-(leaving group substituted)-1-(alk-2-enyl)silyl-2-azetidinone (III) is treated with acid e.g., zinc bromide to obtain 4-(alk-2-enyl)-2-azetidinone (IV).

The 4-(alk-2-enyl)-2-azetidinone (IV) can be converted into stereochemically highly pure carbapenems by a known method (e.g., Japanese Patent Application No. 60-260731).

The following illustrates the groups in the formula:

R is hydrogen, optionally substituted alkyl. Representative are well known in carbapenem and penem compounds including hydrogen, 1 C to 8 C alkyl (e.g., methyl, ethyl, propyl), 1 C to 8 C hydroxyalkyl (e.g., hydroxymethyl, 1-hydroxyethyl, 1-hydroxypropyl, 2-hydroxyisopropyl), 1 C to 8 C haloalkyl (e.g., fluoromethyl, chloromethyl, 1-fluoroethyl, 2-fluoroisopropyl, trifluoromethyl), and the like. The hydroxy in the said hydroxyalkyl can be protected conventionally by the following hydroxy protective group, for example, 1 C to 8 C acyl, oxycarbonyl which is a group of carbonic acid half ester (with e.g., 2 C to 10 C alkyl, chloroalkyl, benzyl, o- or p-nitrobenzyl, p-methoxybenzyl, allyl, or the like), 2 C to 8 C ether forming group (e.g., methoxymethyl, methoxyethoxymethyl, tetrahydrofuranyl, tetrahydropyranyl), 3 C to 18 C silyl (e.g., trimethylsilyl, triethylsilyl, dimethylphenylsilyl, diphenyl-t-butylsilyl, triphenylsilyl, dimethyl-t-pentylsilyl), 7 C to 19 C reactive aralkyl (e.g., triphenylmethyl), and the like.

$R^1$ is a leaving group. Representative are hydroxy, optionally substituted 1 C to 8 C alkanoyloxy, 7 C to 15 C aroyloxy, 1 C to 8 C alkylsulfinyl, 6 C to 10 C arylsulfinyloxy, 1 C to 8 C alkylsulfonyloxy, 6 C to 10 C arylsulfonyloxy, halogen (e.g., chlorine, fluorine, bromine), and the like.

$R^2$ and $R^3$ each is hydrogen, optionally substituted alkyl, or aryl. Representative are 1 C to 8 C alkyl (e.g., methyl, ethyl, propyl), 6 C to 8 C monocyclic aryl (e.g., phenyl, tolyl), and the like optionally substituted by, e.g., the oxygen-, sulfur-, or nitrogen-function as explained below including nitrile, isonitrile, halogen, and the like.

$R^4$ is hydrogen, alkyl, or substituted alkyl. Representative are hydrogen, 1 C to 8 C alkyl substituted by a nucleophilic group known as a 3-substituents of cephalosporins, e.g., 1 C to 19 C nucleophilic group, for example, halogen=halo (e.g., fluoro, chloro, bromo, iodo),
oxygen function=hydroxy, 1 C to 8 C alkoxy, 6 C to 10 C aryloxy, 1 C to 10 C acyloxy (e.g., alkanoyl, substituted alkanoyl, aroyl, carbamoyl, substituted carbamoyl, mono- or di-alkylcarbamoyl), 7 C to 19 C aralkoxy (e.g., p-methoxybenzyloxy, benzhydryloxy, trityloxy), oxo, or the like;
sulfur function=6 C to 10 C arylthio (e.g., phenyl, naphthyl, indenyl) the, mono- or di-cyclic heterocyclylthio (furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuryl, benzothienyl, benzoimidazolyl, benzothiazolyl, benzopyrazinyl, quinolyl, pyridopyridyl) thio, 1 C to 8 C alkylthio (e.g., ethyl, fluoroethyl, fluorovinyl), or the like;
nitrogen function=amino, 1 C to 8 C mono- or di-alkylamino, tetrazol-1-yl, triazol-1-yl, 1 C to 10 C mono-or poly-cyclic nitrogen-containing arylinio (e.g., pyridinio, carboxypyridinio, carbamoylpyridinio, picolinio, cyclopentenopyridinio, cyclohexenopyridinio, quinolinio, 1-lower alkylimidazolidinio, cycloalkanopyridinio, 1-lower alkyltriazolidinio, piperidinio, pyrrolidinio, quinuclidinio), or the like;
carbon function=1 C to 8 C alkyl (e.g., methyl, methoxymethyl, ethyl, ethoxymethyl, iodoethyl, propyl, isopropyl, butyl, isobutyl, ethoxyethyl, methylthioethyl, methanesulfonylethyl, trichloroethyl, t-butyl), 3 C to 12 C alkenyl (e.g., propenyl, allyl, prenyl, hexenyl, phenylpropenyl, dimethylhexenyl, 2-oxo-1,3-dioxolylmethyl), 7 C to 19 C aralkyl (e.g., benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl), 6 C to 12 C aryl (e.g., phenyl, tolyl, diisopropylphenyl, xylyl, trichlorophenyl, pentachlorophenyl, indanyl), carboxy, 1 C to 8 C alkyloxycarbonyl where alkyl is, e.g., methyl, methoxymethyl, ethyl, ethoxymethyl, iodoethyl, propyl, isopropyl, butyl, isobutyl, ethoxyethyl, methylthioethyl, methanesulfonylethyl, trichloroethyl, t-butyl; 3 C to 12 C alkenyloxycarbonyl, in which alkenyl is, e.g., propenyl, allyl, prenyl, hexenyl, phenylpropenyl, dimethylhexenyl, 2-oxo-1,3-dioxolylmethyl; 8 C to 20 C aralkoxycarbonyl where aralkyl is, e.g., benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl; 6 C to 12 C aryloxycarbonyl where is, e.g., phenyl, tolyl, diisopropylphenyl, xylyl, trichlorophenyl, pentachlorophenyl, indanyl; 1 C to 12 C aminooxycarbonyl (forming an ester with e.g., acetone oxime, acetophenone oxyme, acetaldoxime, N-hydroxysuccinimide, N-hydroxyphthalimide), 3 C to 12 C silyloxycarbonyl where silyl is, e.g., trimethylsilyl, dimethylmethoxysilyl, t-butyldimethylsilyl, 3 C to 12 C stannyloxycarbonyl where stannyl is trimethylstannyl; 2 C to 15 C 1-oxygenated alkoxycarbonyl where 1-oxygenated alkyl is, for example, straight, branched, cyclic or partly cyclic alkanoyloxyalkyl (e.g., acetoxymethyl, acetoxyethyl, propionyloxymethyl, pivaloyloxymethyl, cyclohexanecarbonyloxyethyl), 3 C to 15 C 1-alkoxycarbonyloxyalkyl (e.g., ethoxycarbonyloxyethyl, isopropoxycarbonyloxyethyl, t-butoxycarbonyloxyethyl, isopentyloxycarbonyloxypropyl, cyclohexylmethoxycarbonyloxyethyl, bornyloxycarbonyloxymethyl), 2 C to 8 C alkoxyalkyl (e.g., methoxymethyl, methoxyethyl), 4 C to 8 C 2-oxacycloalkyl (e.g., tetrahydrofuranyl, tetrahydropyranyl), or the like.

$R^5$ and $R^6$ are the same or different and can be hydrogen, optionally substituted alkyl or aryl, or optionally protected carboxy. Representative are 1 C to 10 C alkyl (e.g., methyl, ethyl, propyl, isopropyl, cyclopropyl, butyl, isobutyl, t-butyl, cyclobutyl, cyclopropylmethyl, pentyl, isopentyl, neopentyl, cyclopentyl, cyclopropylethyl, hexyl, cyclohexyl, cyclopentylmethyl, heptyl, cycloheptyl, cyclopentylethyl, cyclohexylmethyl, octyl, cyclooctyl, cyclohexylethyl, nonyl, dodecyl), carboxy, protected carboxy [for example, 2 C to 10 C alkyl ester (e.g., methyl, ethyl, propyl, isopropyl, cyclopropyl, butyl, isobutyl, t-butyl, cyclobutyl, cyclopropylmethyl, pentyl) ester, substituted alkyl ester (e.g., chloroethyl, methanesulfonylethyl ester), aralkyl ester (e.g., benzyl, p-nitrobenzyl, p-methoxybenzyl, o-nitrobenzyl), or alkenyl ester (e.g., prenyl, allyl) ester forming protected carboxy], and the like.

$R^7$ and $R^8$ are the same or different and can be hydrogen, halogen, or optionally substituted alkyl or aryl. Representative are 1 C to 8 C alkyl (e.g., methyl, ethyl, propyl, isopropyl, cyclopropyl, butyl, isobutyl, t-butyl, cyclobutyl, cyclopropylmethyl, pentyl, isopentyl, neopentyl, cyclopentyl, cyclopropylethyl, hexyl, cyclohexyl), 1 C to 8 C substituted alkyl (e.g., chloroethyl, methanesulfonylethyl), 1 to 10 C mono- or di-cyclic 5 to 6 membered ring carbo- or hetero-cyclic aryl (e.g., phenyl, naphthyl, indenyl, furyl, thienyl, pyrrolyl, oxazolyl, thiazolyl, imidazolyl, oxadiazolyl, thiadiazolyl, triazolyl, thiatriazolyl, tetrazolyl, pridyl, pyranyl, indolyl, benzofuryl, benzothienyl, benzoimidazolyl, benzothiazolyl, benzothienyl, benzoimidazolyl, benzothiazolyl, benzopyradinyl, quinolyl, pyridopyridyl), halogen (e.g., fluorine, chlorine, bromine, iodine, pseudohalogen), and the like.

Hal is halogen. Representative are chlorine, bromine, and iodine, and including a pseudohalogen (e.g., lower alkanesulfonyloxy, benzenesulfonyloxy, substituted benzenesulfonyloxy).

The said $R^2$, $R^3$, $R^4$, $R^5$, and $R^6$ can be combined directly or through a hetero atom to form a part of cyclic structure.

The substituent in the said R, $R^1$, $R^2$, $R^3$, $R^4$, $R^5$, $R^6$, $R^7$ and $R^8$ 1 or more the same or different substituents. It may be one of the substituents as given below.

The alkyl part of the said groups is straight, branched or cyclic alkyl. Representative alkyls are methyl, ethyl, propyl, isopropyl, cyclopropyl, butyl, isobutyl, t-butyl, cyclobutyl, cyclopropylmethyl, pentyl, isopentyl, neopentyl, cyclopentyl, cyclopropylethyl, hexyl, cyclohexyl, cyclopentylmethyl, heptyl, cycloheptyl, cyclopentylethyl, cyclohexylmethyl, octyl, cyclooctyl, cyclohexylethyl, nonyl, dodecyl, and the like. These may have a substituent as illustrated below.

The aralkyl part of the groups is a combination of a alkyl part and aryl part. Representative aralkyls are benzyl, phenylethyl, phenylpropyl, phenylisopropyl, naphthylmethyl, furylmethyl, thienylpropyl, oxazolylmethyl, thiazolylmethyl, imidazolylmethyl, triazolylmethyl, pyridylmethyl, indolylmethyl, benzoimidazolylethyl, benzothiazolylmethyl, quinolylmethyl, and the like. These may have a substituent as illustrated below.

The acyl part of the groups is a straight, branched, or cyclic alkanoyl, mono- or di-cyclic, optionally heterocyclic aroyl, aralkanoyl, arylalkenoyl, alkylsulfonyl, arylsulfonyl, carbamoyl, carbalkoxy, carbaralkoxy, sulfo, and the like acyl groups. These acyl may have a substituent as illustrated at the item of alkyl.

The aryl part is mono- or di-cyclic 5- to 6-membered carbo- or hetero-cyclic aryl. This heterocyclic group may have oxygen, nitrogen, or sulfur as a heteroatom. Representative aryls are phenyl, naphthyl, indenyl, furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuryl, benzothienyl, benzoimidazolyl, benzothiazolyl, benzopyradinyl, quinolyl, pyridopyridyl, and the like. These may have a substituent as illustrated below.

The representative substituents which can be combined with the said groups include a carbon function (e.g., straight, branched, or cyclic alkyl, alkenyl, alkinyl, aralkyl, aryl, heterocyclyl, carboxylic acyl, carbamoyl, carboxy, protected carboxy, cyano), nitrogen function (e.g., amino, acylamino, guanidyl, ureido, alkylamino, dialkylamino, isothiocyano, isocyano, nitro, nitroso), oxygen function (e.g., hydroxy, alkoxy, aryloxy, heterocyclyloxy, cyanato, oxo, carboxylic acyloxy, sulfonic acyloxy, phosphoric acyloxy), sulfur function (e.g., mercapto, alkylthio, alkylsulfonyl, arylthio, arylsulfonyl, heterocyclylthio, heterocyclysulfonyl, acylthio, thioxo, sulfo, sulfamoyl), halogen (e.g., fluoro, chloro, bromo, iodo), silyl (e.g., trialkylsilyl, dialkylalkoxysilyl), and stannyl (e.g., trialkylstannyl). The said carbon numbers do not include that of protective group.

THE REACTIONS OF THIS INVENTION (1) N-Silyl Introduction

The reaction of 4-(leaving group substituted)-2-azetidinone (I) with (alk-2-enyl)halosilane (II) in an inert solvent (e.g., hydrocarbon, ether, ester, halohydrocarbon solvent) in the presence of a condensing reagent affords the corresponding 4-(leaving group substituted)-1-(alk-2-enyl)silyl-2-azetidinone (III). Generally, the reaction of 4-(leaving group substituted)-2-azetidinone (I) with 1 to 2 equivalents of (alk-2-enyl)halosilane (II) at −20° to 40° C. completes within a time between 30 minutes and 25 hours. The yield is about 80 to 95%.

Here, the condensing reagent can preferably be 1 to 5 equivalents of a tertiary amine, for example, tri(1 C to 8 C alkyl)amine (e.g., triethylamine, tri(2-hydroxyethyl)amine, triton B, N,N-dimethylaniline), an aromatic base (e.g., pyridine, picoline, lutidine, nicotine), a weakly basic anion exchenage resin (e.g., Amberlite IR-45, IR-4B, Duorite A-4), a metal oxide, an alkali metal aliphatic or aromatic carboxylate (e.g., formate, acetate, phenylacetate, benzoate), or the like bases as far as the production of the objective material is not disturbed.

(2) Rearrangement

By the action of acid on 4-(leaving group substituted)-1-(alk-2-enyl)silyl-2-azetidinone (III) in an inert solvent (e.g., hydrocarbon, ether, ester, halohydrocarbon solvent), the intramolecular allylic rearrangement occurs to give the corresponding 4-(alk-2-enyl)-2-azetidinone (IV). Usually, the reaction at −40° to 40° C. completes within a time between 1 and 24 hours. The yield is about 80 to 90%.

Here, the acid can preferably be 0.1 to 5 equivalents of a mineral acid (e.g., hydrochloric acid, phosphoric acid, sulfuric acid, nitric acid, perchloric acid), carboxylic acid (e.g., formic acid, acetic acid, malic acid, trifluoroacetic acid), sulfonic acid (e.g., methanesulfonic acid, trifluoromethanesulfonic acid, benzenesulfonic acid, toluenesulfonic acid, trifluoromethanesulfonic acid trimethylsilyl ester), Lewis acid (e.g., aluminum chloride, zinc chloride, zinc bromide, titanium chloride, stannic chloride, antimony chloride, cupper acetate) or the like.

As is explained above, the C to C bond formation is a novel reaction specific to the intramolecular reaction of 4-leaving group substituted-1-(substituted or unsubstituted allyl)silyl-2-azetidinone, unattainable by the intermolecular reaction.

REACTION CONDITION

The said synthetic reactions are carried out usually at −20° to 50° C. for 10 minutes to 10 hours. It is carried out in a solvent, if required under anhydrous condition. Other conventional conditions can be applied similarly.

The solvent for the reactions is, for example, hydrocarbon (e.g., pentane, hexane, octane, benzene, toluene, xylene), halogenohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethylsulfoxide), carboxylic acid (e.g., formic acid, acetic acid, propionic acid), organic base (e.g., diethylamine, triethylamine, pyridine, picoline, collidine, quinoline), alcohol (e.g, methanol, ethanol, propanol, hexanol, octanol, benzyl alcohol), water, or the like industrial solvents or mixtures thereof.

WORK UP

The objective products can be obtained from the reaction mixture by removing contaminants (e.g., unreacted starting material, by-products, solvent) in a conventional manner (e.g., extracting, evaporating, washing, concentrating, precipitating, filtering, drying) and isolated by a conventional work up (e.g., absorption, elution, distillation, precipitation, chromatography), or a combination of these.

USE

The product, 4-alkenyl-2-azetidinone, can be used for producing, at least some known antibacterials. Thus, 4-(alk-2-enyl)-2-azetidinone (IV) can be converted into 1β-methyl-2-(nucleophilic group substituted)methylcarbapenem (VIII) efficiently by the route as shown in the scheme on the next page wherein Het is 1,2,4-thiadiazolyl; $R^9$ is 1-t-butyldimethylsilyloxyethyl; and $R^{10}$ is p-nitrobenzyl in a representative case.

Namely, 4-(alk-2-enyl)-2-azetidinone (IV) is treated with p-nitrobenzyl glyoxylate (1.5 equivalents) in tetrahydrofuran in the presence of triethylamine at about 50° C. for 3 hours to give glycolate (V). This is treated with m-chloroperbenzoic acid (2 equivalents) and sodium hydrogen carbonate (2 equivalents) giving epoxide which is then treated with thionlyl chloride (1.2 equivalents) and lutidine (3 equivalents) at −20° C. for 1.5 hours in tetrahydrofuran, and then reacted with in dioxane with triphenylphosphine (1.2 equivalents) and lutidine (3 equivalents) at 60° C. for 5 hours to give ylide (VI). This is reacted with 1,2,4-thiadiazolylthiol (3 equivalents) and butyllithium (0.5 equivalents) in tetrahydrofuran to give thiolate (VII).

This is oxidized using dimethyl sulfoxide (3 equivalents), trifluoroacetic acid anhydride (2 equivalents), and trietylamine (4.5 equivalents) in dichloromethane to give the corresponding ketone and then the product is heated in toluene to form the carbapenem ring, and deesterified in dichloromethane with aluminum chloride to give 1β-methyl-2-(nucleophilic group substituted)methylcarbapenem compound (VIII).

The antibacterial potency of the objective 1β-methyl isomer is superior to that of the corresponding 1α-methyl isomer.

Similarly, 4-(alk-2-enyl)-2-azetidinone (IV) can also be converted into sterically pure 1β-methyl-2-nucleophilic group substituted-carbapenem compound (IX).

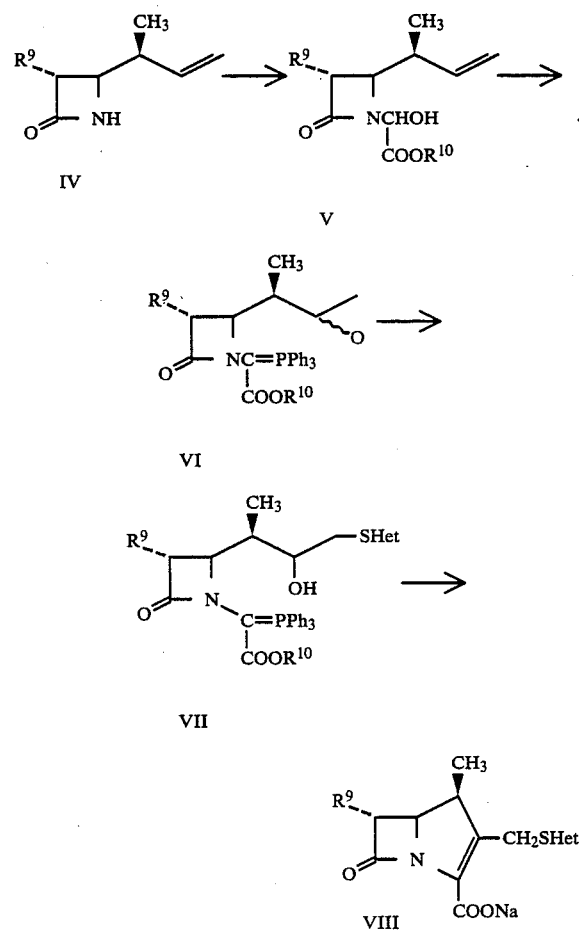

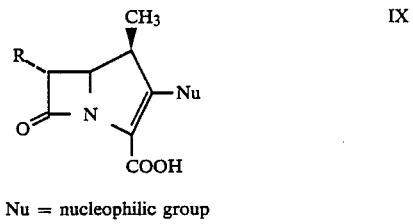

Nu = nucleophilic group

The following examples show the embodiment of this invention. In the NMR of a compound having more than one same type groups and when the chemical shifts of protons in them are different, the signal splits and the area ratio corresponds to number of the group and total area corresponds to number of the protons. In this case each chemical shift is shown with comma and number of splitting and the mark "x" are given before the type of the signals.

(Abbreviations) Ac=acetyl, tBu=t-butyl, Bz=benzoyl, Dioxolon-Et=2-oxo-4-methyl-1,3-dioxol-4-yl, Et=ethyl, Me=methyl, Ms=mesyl, PMB=p-methoxybenzyl, PNB=p-nitrobenzyl, Ph=phenyl, Pro=propionyl, Tet=1-methyltetrazol-5-yl, Tdz=thiadiazolyl, THP=tetrahdropyranyl, Tr=trityl, Ts=tosyl.

EXAMPLE 1

Intermediates for Producing 1β-Methylcarbapenems from the 4-Acetoxyazetidinone Starting Material

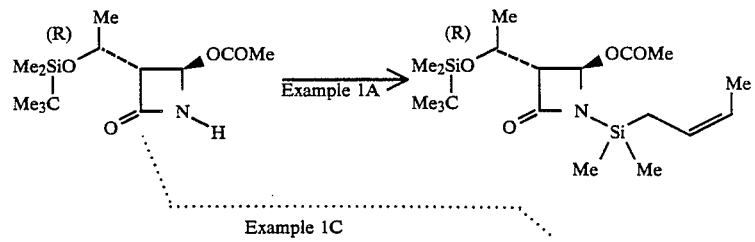

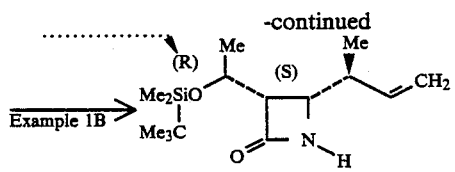

EXAMPLE 1A

To an ice cold solution of 3α-(1-(R)-t-butyldimethyl-silyloxyethyl)-4β-acetoxyazetidin-2-one (10.01 g; 34.83 millimoles) and (Z)-crotyldimethylchlorosilane (5.71 g; 1.1 equivalents) in dichloromethane (30 ml) are added dropwise triethylamine (5.6 ml; 1.15 equivalents) with stirring. After 30 minutes' stirring, the mixture is kept at room temperature overnight, diluted with hexane (300 ml) and precipitating triethylamine hydrochloride salt is removed by filtration. The filtrate is concentrated in vacuum to give 1-(Z)-crotyldimethylsilyl-3α-(1-(R)-t-butyldimethylsilyloxyethyl)-4β-acetoxyazetidin-2-one (14.0 g).

NMR (EM-390, CDCl$_3$)δ: 0.07, 0.13, 0.25(3xs, 12H), 0.89(s, 9H), 1.23(d, J=6.5 Hz,3H), 1.57(d, J=4.5 Hz, 3H), 1.75(d, J=7 Hz, 3H), 2.07 (s, 3H), 3.15(d-like, 1H), 4.21(m, 1H), 5.23~5.57(m, 2H), 6.15(s, 1H) ppm.

IR (Nujol)ν: 1756, 1750, 1654, 1260, 1236, 840 cm$^{-1}$.

NMR (VR-200, CDCl$_3$)δ: 0.06, 0.08, 0.24, 0.27(4xs, 12H), 0.88(s, 9H), 1.24(d, J=6.4 Hz, 3H), 1.58(d, J=5 Hz, 3H), 1.75(d, J=7.2 Hz, 2H), 2.09(s, 3H), 3.14(dd-like, 1H), 4.19(m, 1H), 5.31~5.53(m, 2H), 6.14 (s, 1H) ppm.

EXAMPLE 1B

To a solution of 3α-(1-(R)-t-butyldimethylsilyloxyethyl)-4β-acetoxy-1-(Z)-(crotyldimethylsilyl)azetidin-2-one (5.24 g; 13.1 millimoles) in dichloromethane (18 ml) at −20° C. with stirring is dropwise added trifluoromethanesulfonic acid trimethylsilyl ester (1.26 ml; 0.5 equivalents). After 10 minutes, the mixture is kept at room temperature for 1.5 hours. The reaction mixture is poured into cold aqueous sodium hydrogen carbonate and the organic layer is separated, dried, and concentrated in vacuum. The residue is recrystallized from n-hexane to give 3α-(1-(R)-t-butyldimethylsilyloxyethyl)-4β-((R)-1-buten-3-yl)azetidin-2-one (2.81 g) showing physical constants identical with those of literatures. mp 142°-142.5° C. Yield: 75.7%.

By chromatographic separation of the mother liquor on silica gel (Lober-B: toluene/ethyl acetate=2:1), further crystals of above product (130 mg; yield: 3.5%) from non-polar fraction and 3α-(1-(R)-t-butyldimethyl-silyloxyethyl)-4β-((S)-1-buten-3-yl)azetidin-2-one (1:1 mixture; 206 mg; Yield: 5.6%). The latter mixture gives crystals of each isomers on repeated silica gel chromatography.

NMR (VR-200, CDCl$_3$)δ: 0.07(s, 6H), 0.88 (s, 9H), 1.09(d, J=6.8 Hz, 3H), 1.18(d, J=6.2 Hz, 3H), 2.33(m, 1H), 2.81(brs, 1H), 3.50 (dd, J=7.5 Hz, J=2.0 Hz, 1H), 4.17(m, 1H), 5.05-5.15(m, 2H), 5.69-5.86(m, 1H), 5.97(brs, 1H) ppm.

IR (Nujol)ν: 1758, 1712, 1642, 1051, 830 cm$^{-1}$.

EXAMPLE 1C (1 Step Reaction (1))

To a cold stirred solution of 3α-(1-(R)-t-butyldimethylsilyloxyethyl)-4β-acetoxyazetidin-2-one (900 mg; 3.13 millimoles) and (Z)-crotyldimethylchlorosilane (560 mg; 1.2 equivalents) in dichloromethane (4.5 ml) is dropwise added triethylamine (0.53 ml) (1.2 equivalents). After keeping at room temperature overnight, zinc bromide (740 mg; 1.05 equivalents) is added to the reaction mixture and it is stirred at room temperature for 24 hours. The reaction mixture is poured into cold aqueous sodium hydrogen carbonate. The organic layer is separated, dried, and concentrated in vacuum. The crystals are recrystallized from acetonitrile to give 3α-(1-(R)-t-butyldimethylsilyloxyethyl)-4β-((R)-1-buten-3-yl)azetidin-2-one (355 mg). mp 140°-142° C. Yield: 40.0%.

EXAMPLE 2

Intermediates for Producing 1β-Methylcarbapenems from 4-Benzoyloxyazetidinone Starting Material (1 Step Reaction (2))

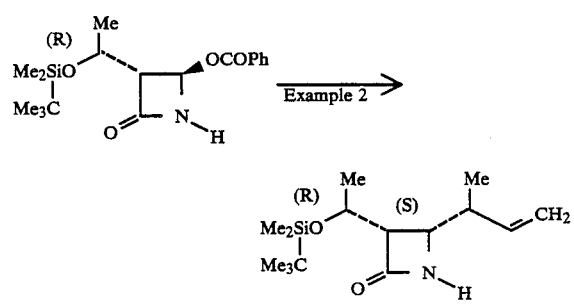

To an ice cold stirred solution of 3α-(1-(R)-t-butyl-dimethylsilyloxyethyl)-4β-benzoyloxyazetidin-2-one (365 mg) and (Z)-crotyldimethylchlorosilane (185 mg; 1.2 equivalents) in a chloroform-benzene mixture (3:1; 1.5 ml) is dropwise added triethylamine (0.18 ml; 1.2 equivalents). After stirring at room temperature overnight, the solution is mixed with zinc bromide (243 mg) and stirred at room temperature for 24 hours. The reaction mixture is poured into aqueous sodium hydrogen carbonate. The organic layer is taken, dried, and concentrated in vacuum. The residue is crystallized from acetonitrile to give 3α-(1-(R)-t-butyldimethylsilyloxyethyl)-4β-((R)-1-buten-3-yl)azetidin-2-one (178 mg). mp 140°-142° C. Yield: 61.2%.

EXAMPLE 3

Intermediate for Producing 1-Unsubstituted Carbapenems from 4-Acetoxyazetidinone Starting Material

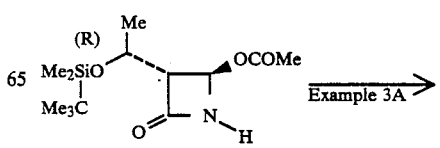

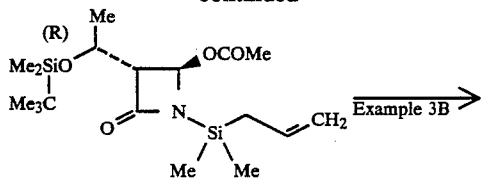

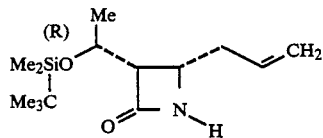

EXAMPLE 3A

A solution of 3α-(1-(R)-t-butyldimethylsilyloxyethyl)-4β-acetoxyazetidin-2-one (287 mg; 1 millimoles), allyldimethylchloro silane 190 mg (1.4 equivalents), and triethylamine (0.2 ml) in dichloromethane (2 ml) is kept at room temperature overnight. The reaction mixture is diluted with dichloromethane, washed with aqueous sodium hydrogen carbonate, dried, and concentrated in vacuum to give 3α-(1-(R)-t-butyldimethylsilyloxyethyl)-4β-acetoxy-1-(allyldimethylsilyl)azetidin-2-one (450 mg).

NMR (VR-200, CDCl$_3$)δ: 0.06, 0.07, 0.26, 0.28(4xs, 12H), 0.87(s, 9H), 1.23(d, J=6.5 Hz, 3H), 1.77(d, J=7 Hz, 2H), 2.09(s, 3H), 3.15 (dd, J=3 Hz, J=1.3 Hz, 1H), 4.18 (m, 1H), 4.82–4.98(m, 2H), 5.66–5.88(m, 1H), 6.13(d, J=1.3 Hz, 1H) ppm.

IR (film)ν: 1740–1780, 1636, 1230, 840 cm$^{-1}$.

EXAMPLE 3B

To a solution of 3α-(1-(R)-t-butyldimethylsilyloxyethyl)-4β-acetoxy-1-(allyldimethylsilyl)azetidin-2-one (450 mg) in dichloromethane (2 ml) is added trifluoromethanesulfonic acid trimethylsilyl ester (60 μl) under ice cooling. After stirring for 1 hour at room temperature, the reaction mixture is diluted with dichloromethane, washed with aqueous sodium hydrogen carbonate, dried, and concentrated to give 3α-(1-(R)-t-butyldimethylsilyloxyethyl)-4β-allylazetidin-2-one (240 mg) showing physical constants the same as those of literature. Yield: 90%.

EXAMPLE 4

Similar Reactions

Under a condition similar to that of Examples from 1 to 3, 4-(leaving group substituted)-1-(alk-2-enyl)silyl-2-azetidinone (III) and 4-(alk-2-enyl)-2-azetidinone (IV) having the groups as given on Table 1 (1) to (3) below are prepared from the corresponding 4-(leaving group substituted)-2-azetidinone (I).

TABLE 1

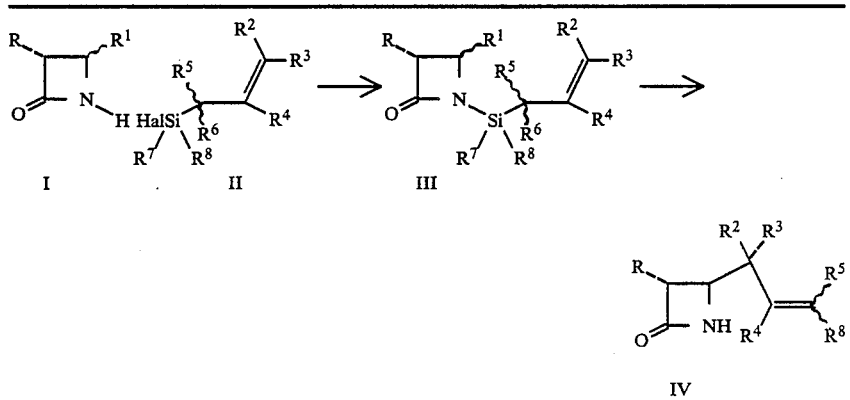

| R | R$^1$ | R$^2$ | R$^3$ | R$^4$ | R$^5$ | R$^6$ | R$^8$ | R$^8$ |
|---|---|---|---|---|---|---|---|---|
| Me | AcO | H | H | H | H | H | Me | Me |
| Me | AcO | Me | H | H | H | H | Me | Me |
| AcO-Me | AcO | Me | H | H | H | H | Me | Me |
| tBuMe$_2$SiO-Me | AcO | H | H | H | H | H | Me | Me |
| tBuMe$_2$SiO-Me | AcO | Me | H | H | H | H | Me | Me |
| Et | AcO | H | H | H | H | H | Me | Me |
| Et | AcO | Me | H | H | H | H | Me | Me |
| Et | AcO | Et | H | H | H | H | Me | Me |
| Et | AcO | Me | H | CH$_2$STet | H | H | Me | Me |
| Et | AcO | Me | H | CH$_2$CH$_2$Cl | H | H | Ph | Ph |
| Et | AcO | Me | H | CH$_2$CH$_2$OAc | H | H | Ph | Ph |
| Et | AcO | Me | H | CH$_2$CH$_2$COOPNB | Ph | Ph | Me | Me |
| 1-F-Et | AcO | H | H | H | H | H | Me | Me |
| 1-F-Et | AcO | Me | H | H | H | H | Me | Me |
| 1-F-Et | AcO | Me | H | CH$_2$CH$_2$COOPNB | Ph | Ph | Me | Me |
| 1-Cl-Et | AcO | Me | H | H | H | H | Me | Me |
| 1-PNBOCOO-Et | AcO | H | H | H | H | H | Me | Me |
| 1-PNBOCOO-Et | AcO | Me | H | H | H | H | Me | Me |
| 1-PNBOCOO-Et | AcO | Me | Me | H | H | H | Ph | Ph |
| 1-PNBOCOO-Et | AcO | Me | H | CH$_2$CH$_2$Cl | H | H | Me | Me |
| 1-Me$_3$SiO-Et | HO | Me | H | H | H | H | Me | Me |
| 1-Me$_3$SiO-Et | Cl | Me | H | H | H | H | Me | Me |
| 1-Me$_3$SiO-Et | AcO | H | H | H | H | H | Me | Me |
| 1-Me$_3$SiO-Et | AcO | Me | H | H | H | H | Me | Me |
| 1-tBuMe$_2$SiO-Et | HO | Me | H | H | H | H | Me | Me |
| 1-tBuMe$_2$SiO-Et | AcO | H | H | H | H | H | Me | Me |

TABLE 1-continued

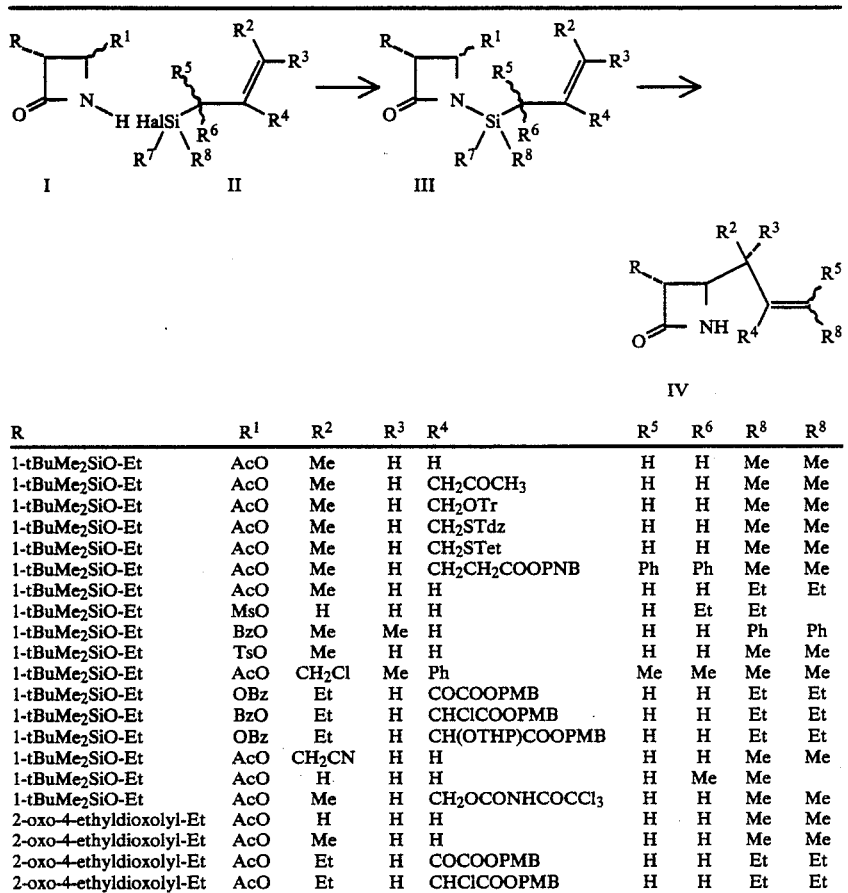

| R | R¹ | R² | R³ | R⁴ | R⁵ | R⁶ | R⁷ | R⁸ |
|---|---|---|---|---|---|---|---|---|
| 1-tBuMe₂SiO-Et | AcO | Me | H | H | H | H | Me | Me |
| 1-tBuMe₂SiO-Et | AcO | Me | H | CH₂COCH₃ | H | H | Me | Me |
| 1-tBuMe₂SiO-Et | AcO | Me | H | CH₂OTr | H | H | Me | Me |
| 1-tBuMe₂SiO-Et | AcO | Me | H | CH₂STdz | H | H | Me | Me |
| 1-tBuMe₂SiO-Et | AcO | Me | H | CH₂STet | H | H | Me | Me |
| 1-tBuMe₂SiO-Et | AcO | Me | H | CH₂CH₂COOPNB | Ph | Ph | Me | Me |
| 1-tBuMe₂SiO-Et | AcO | Me | H | H | H | H | Et | Et |
| 1-tBuMe₂SiO-Et | MsO | H | H | H | H | H | Et | Et |
| 1-tBuMe₂SiO-Et | BzO | Me | Me | H | H | H | Ph | Ph |
| 1-tBuMe₂SiO-Et | TsO | Me | H | H | H | H | Me | Me |
| 1-tBuMe₂SiO-Et | AcO | CH₂Cl | Me | Ph | Me | Me | Me | Me |
| 1-tBuMe₂SiO-Et | OBz | Et | H | COCOOPMB | H | H | Et | Et |
| 1-tBuMe₂SiO-Et | BzO | Et | H | CHClCOOPMB | H | H | Et | Et |
| 1-tBuMe₂SiO-Et | OBz | Et | H | CH(OTHP)COOPMB | H | H | Et | Et |
| 1-tBuMe₂SiO-Et | AcO | CH₂CN | H | H | H | H | Me | Me |
| 1-tBuMe₂SiO-Et | AcO | H | H | H | H | Me | Me | |
| 1-tBuMe₂SiO-Et | AcO | Me | H | CH₂OCONHCOCCl₃ | H | H | Me | Me |
| 2-oxo-4-ethyldioxolyl-Et | AcO | H | H | H | H | H | Me | Me |
| 2-oxo-4-ethyldioxolyl-Et | AcO | Me | H | H | H | H | Me | Me |
| 2-oxo-4-ethyldioxolyl-Et | AcO | Et | H | COCOOPMB | H | H | Et | Et |
| 2-oxo-4-ethyldioxolyl-Et | AcO | Et | H | CHClCOOPMB | H | H | Et | Et |

What is claimed is:

1. A process for preparing a 4(alk-2-enyl)-2-azetidinone of the formula (IV) which comprises treating a 4-(leaving group substituted)-1-(alk-2-enyl) silyl-2-azetidinone of the formula (III) with an acid in an inert solvent, said formulas III and IV being as follows:

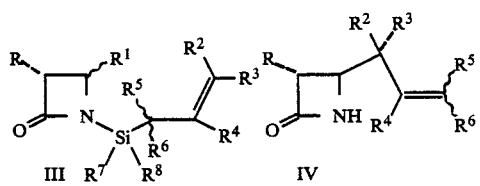

wherein R is hydrogen, alkyl, alkyl substituted by hydroxy, protected hydroxy or alkyl substituted by one halogen, R¹ is a leaving group, R² is alkyl, aryl, substituted alkyl or substituted aryl in which the substituents on the alkyl or aryl groups are selected from the group consisting of hydroxy, 1 C to 8 C alkoxy, 6 C to 10 C aryloxy, 1 C to 10 C acyloxy, 7 C to 19 C aralkoxy, oxo, 6 C to 10 C arylthio, furylthio, thienylthio, pyrrolylthio, oxazolylthio, thiazolylthio, imidazolylthio, oxadiazolylthio, thiadiazolylthio, triazolylthio, thiatriazolylthio, tetrazolylthio, pyridylthio, pyranylthio, indolylthio, benzofurylthio, benzothienylthio, benzoimidazolylthio, benzothiazolylthio, benzopyrazinylthio, quinolylthio, pyridopyridylthio, 1 C to 8 C alkylthio, amino, 1 C to 8 C mono- or di-alkylamino, tetrazol-1-yl, triazol-1-yl, halogen, nitrile and isonitrile, R³ is hydrogen, R⁴ is hydrogen, 1 C to 8 C alkyl, 1 C to 8 C alkyl substituted by halogen, oxo, furylthio, thienylthio, pyrrolylthio, oxazolylthio, thiazolylthio, imidazolylthio, oxadiazolylthio, thiadiazolylthio, triazolylthio, thiatriazolylthio, tetrazolylthio, pyridylthio, pyranylthio, indolylthio, benzofurylthio, benzothienylthio, benzoimidazolylthio, benzothiazolylthio, benzopyrazinylthio, quinolylthio, pyridopyridylthio, R⁵ and R⁶ each is hydrogen, alkyl, substituted alkyl, aryl, substituted aryl, carboxy, or protected carboxy, R⁷ and R⁸ each is hydrogen, alkyl, substituted alkyl, aryl or substituted aryl, wherein the substituents on the alkyl and aryl groups in R⁵, R⁶, R⁷ and R⁸ are selected from the group consisting of hydroxy, 1 C to 8 C alkoxy, 6 C to 10 C aryloxy, 1 C to 10 C acyloxy, 7 C to 19 C aralkoxy, 6 C to 10 C arylthio, furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuryl, benzothienyl, benzoimidazolyl, benzothiazolyl, benzopyrazinyl, quinolyl, pyridopyridyl, 1 C to 8 C alkylthio, amino, 1 C to 8 C mono- or di-alkylamino, tetrazol-1-yl, triazol-1-yl, halogen, trialkylsilyl, dialkyl alkoxysilyl and trialkylstannyl.

2. A process as claimed in claim 1 wherein the reaction is carried out with 0.1 to 5.0 equivalents of a mineral acid, carboxylic acid, sulfonic acid, or Lewis acid.

3. A process as claimed in claim 1 wherein the reaction is carried out at between −40° and 40° C.

4. A process as claimed in claim 1 wherein the reaction is carried out over 1 to 24 hours.

* * * * *